US00PP29018P2

(12) United States Plant Patent
Koppe

(10) Patent No.: US PP29,018 P2
(45) Date of Patent: Feb. 27, 2018

(54) ***BEGONIA* PLANT NAMED 'KRBELAT02'**

(50) Latin Name: *Begonia hybrida*
Varietal Denomination: KRBELAT02

(71) Applicant: Lubbertus H. Koppe, Putten (NL)

(72) Inventor: Lubbertus H. Koppe, Putten (NL)

(73) Assignee: Koppe Royalty B.V., Putten (NL)

( * ) Notice: Subject to any disclaimer, the term of this patent is extended or adjusted under 35 U.S.C. 154(b) by 0 days.

(21) Appl. No.: 15/330,208

(22) Filed: Aug. 22, 2016

(51) Int. Cl.
*A01H 5/12* (2006.01)

(52) U.S. Cl.
USPC ..... Plt./343

(58) Field of Classification Search
USPC ..... Plt./343
CPC ..... A01H 5/0238; A01H 5/02; A01H 5/00; A01H 5/12
See application file for complete search history.

*Primary Examiner* — June Hwu
(74) *Attorney, Agent, or Firm* — C. A. Whealy

(57) ABSTRACT

A new and distinct cultivar of *Begonia* plant named 'KRBELAT02' characterized by its upright to broadly spreading and uniformly mounded plant habit; moderately vigorous growth habit; freely branching habit; showy leaves that are green and greyed green in color with centers that are flushed with red purple; and excellent postproduction longevity.

2 Drawing Sheets

Botanical designation: *Begonia hybrida.*
Cultivar denomination: 'KRBELAT02'.

BACKGROUND OF THE INVENTION

The present invention relates to a new and distinct cultivar of *Begonia* plant, botanically known as *Begonia hybrida*, commercially referred to as a Rex *Begonia* and hereinafter referred to by the name 'KRBELAT02'.

The new *Begonia* plant is a product of a planned breeding program conducted by the Inventor in Ermelo, The Netherlands. The objective of the breeding program is to create new Rex *Begonia* plants with unique and attractive leaf coloration.

The new *Begonia* plant originated from a cross-pollination made by the Inventor in Ermelo, The Netherlands in January, 2009 of a proprietary selection of *Begonia hybrida* identified as code number KV06B0370-002, not patented, as the female, or seed, parent with a proprietary selection of *Begonia hybrida* identified as code number KV07B0399-002, not patented, as the male, or pollen, parent. The new *Begonia* plant was discovered and selected by the Inventor as a single flowering plant from within the progeny of the stated cross-pollination in a controlled greenhouse environment in Ermelo, The Netherlands in January, 2010. Asexual reproduction of the new *Begonia* plant by leaf cuttings taken in a controlled greenhouse environment in Ermelo, The Netherlands since February, 2010 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'KRBELAT02'. These characteristics in combination distinguish 'KRBELAT02' as a new and distinct *Begonia* plant:

1. Upright to broadly spreading and uniformly mounded plant habit.
2. Moderately vigorous growth habit.
3. Freely branching habit.
4. Showy leaves that are green and greyed green in color with centers that are flushed with red purple.
5. Excellent postproduction longevity.

Plants of the new *Begonia* differ primarily from plants of the female parent selection in leaf color as plants of the female parent selection have green and dark purple-colored leaves with whitish grey-colored spots. In addition, plants are more vigorous than plants of the female parent selection.

Plants of the new *Begonia* differ primarily from plants of the male parent selection in leaf color as plants of the male parent selection have green and purple-colored leaves with small purple grey-colored spots. In addition, plants are more uniform than plants of the male parent selection.

Plants of the new *Begonia* can be compared to plants of *Begonia hybrida* 'African Jungle', not patented. In side-by-side comparisons, plants of the new *Begonia* differ primarily from plants of 'African Jungle' in leaf color as plants of 'African Jungle' have green-colored leaves with purple grey-colored spots. In addition, plants of the new *Begonia* are more freely branching than plants of 'African Jungle'.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical plant of 'KRBELAT02' grown in a container.

The photograph on the second sheet are close up views of the upper (top of the sheet) and lower (bottom of the sheet) surfaces of typical leaves of 'KRBELAT02'.

DETAILED BOTANICAL DESCRIPTION

The aforementioned photographs and following observations and measurements describe plants grown during the late spring in 12-cm containers in a shaded glass-covered greenhouse in Ermelo, The Netherlands and under cultural practices typical of commercial Rex *Begonia* production. During the production of the plants, day temperatures averaged 20° C. and night temperatures averaged 18° C. Plants were ten weeks old when the photographs and description were taken. In the following description, color references are made to The Royal Horticultural Society Colour Chart, 2015 Edition, except where general terms of ordinary dictionary significance are used.

Botanical classification: *Begonia hybrida* 'KRBELAT02'.

Parentage:

*Female, or seed, parent*.—Proprietary selection of *Begonia hybrida* identified as code number KV06B0370-002, not patented.

*Male, or pollen, parent*.—Proprietary selection of *Begonia hybrida* identified as code number KV07B0399-002, not patented.

Propagation:

*Type*.—By leaf cuttings.

*Time to initiate roots, summer and winter*.—About 20 days at temperatures about 20° C.

*Time to produce a rooted young plant, summer and winter*.—About seven weeks at temperatures about 20° C.

*Root description*.—Fine, fibrous; typically white to orange brown in color, actual color of the roots is dependent on substrate composition, water quality, fertilizer type and formulation, substrate temperature and physiological age of roots.

*Rooting habit*.—Freely branching; medium density; plants of the new *Begonia* have not been observed to form tubers.

Plant description:

*Plant habit and form*.—Upright to broadly spreading and uniformly mounded plant habit; overall plant shape, flattened globular.

*Growth habit*.—Moderately vigorous growth habit and moderate growth rate; suitable for 11-cm and larger containers; under optimal environmental and cultural conditions, usually about eight weeks are required to produce proportional plants in 12-cm containers from rooted leaf cuttings.

*Branching habit*.—Freely branching with about 15 basal branches developing per plant.

*Plant height*.—About 18.5 cm.

*Plant width*.—About 34 cm.

*Lateral branches*.—Length: About 2.4 cm. Diameter: About 5 mm. Internode length: About 1.1 cm. Strength: Moderately strong. Aspect: Erect to about 60° from vertical. Texture: Densely pubescent. Luster: Moderately glossy. Color, developing: Close to 187A. Color, developed: Close to between N186C and 200B.

*Leaves*.—Arrangement: Alternate, simple. Length: About 13.4 cm. Width: About 8.8 cm. Shape: Broadly ovate. Apex: Apiculate. Base: Oblique, lobes slightly overlapping. Margin: Crenate to serrate; strongly undulate. Texture, upper surface: Smooth, glabrous; velvety. Texture, lower surface: Sparsely pubescent along veins; moderately velvety; slightly rugose. Luster, upper surface: Slightly glossy. Luster, lower surface: Matte. Venation pattern: Laciniate. Color: Developing leaves, upper surface: Close to 193A to 193B; towards the margins, close to 146C; leaf edges, close to 187A to 187B. Developing leaves, lower surface: Lighter than between 152D and 195A. Fully expanded leaves, upper surface: Close to between 141A and 143A; mid-section and spots, close to 190A; center, flushed with close to 64B; edges, close to between 187A and 200A; areas surrounding main and secondary veins, close to between 147A and N189A; venation, slightly darker than 148A proximally, close to 64B. Fully expanded leaves, lower surface: Close to between 138B and 148B; edges, close to 187B; areas surrounding main and secondary veins, close to 187B; venation, close to 187B. Petioles: Length: About 11.4 cm. Diameter: About 4.5 mm. Strength: Low, flexible. Texture, upper and lower surfaces: Pubescent. Luster, upper and lower surfaces: Moderately glossy. Color, upper and lower surfaces: Close to between 183B and 187C. Stipules: Length: About 2 cm. Width: About 1 cm. Shape: Narrowly ovate. Apex: Caudate. Base: Broadly cuneate. Margin: Entire. Texture, upper and lower surfaces: Smooth, glabrous. Color, upper and lower surfaces: Close to 60A; towards the margins, close to 53D.

Flower description: Flower initiation and development has not been observed on plants of the new *Begonia*.

Postproduction longevity: Plants of the new *Begonia* are long-lasting and will maintain good quality year-round under interiorscape conditions.

Disease & pest resistance: Resistance to pathogens and pests common to Rex *Begonia* plants has not been observed on plants of the new *Begonia*.

Temperature tolerance: Plants of the new *Begonia* have been observed to tolerate high temperatures of about 35° C. and to be suitable for USDA Hardiness Zones 10 to 12.

It is claimed:

1. A new and distinct *Begonia* plant named 'KRBELAT02' as illustrated and described.

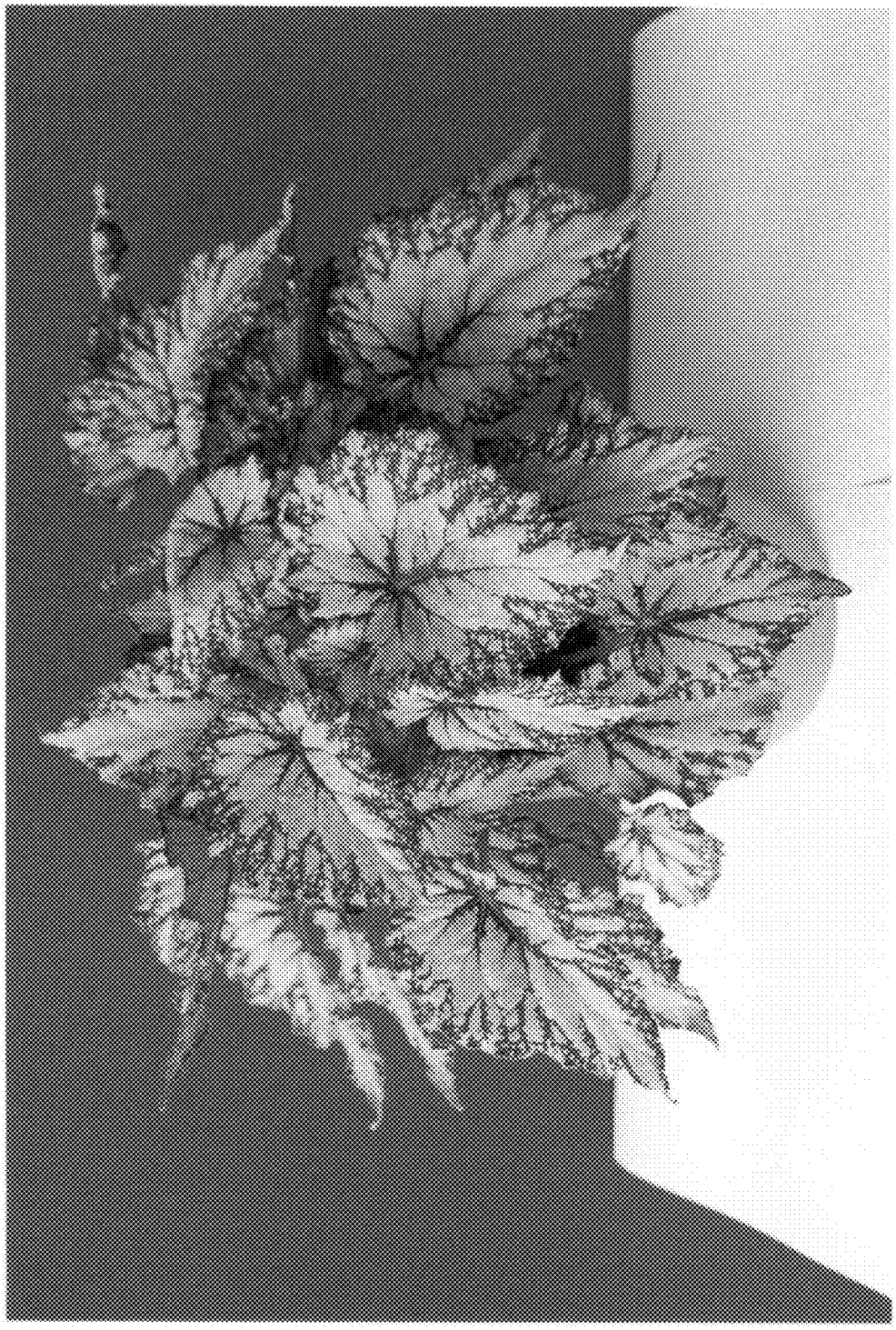

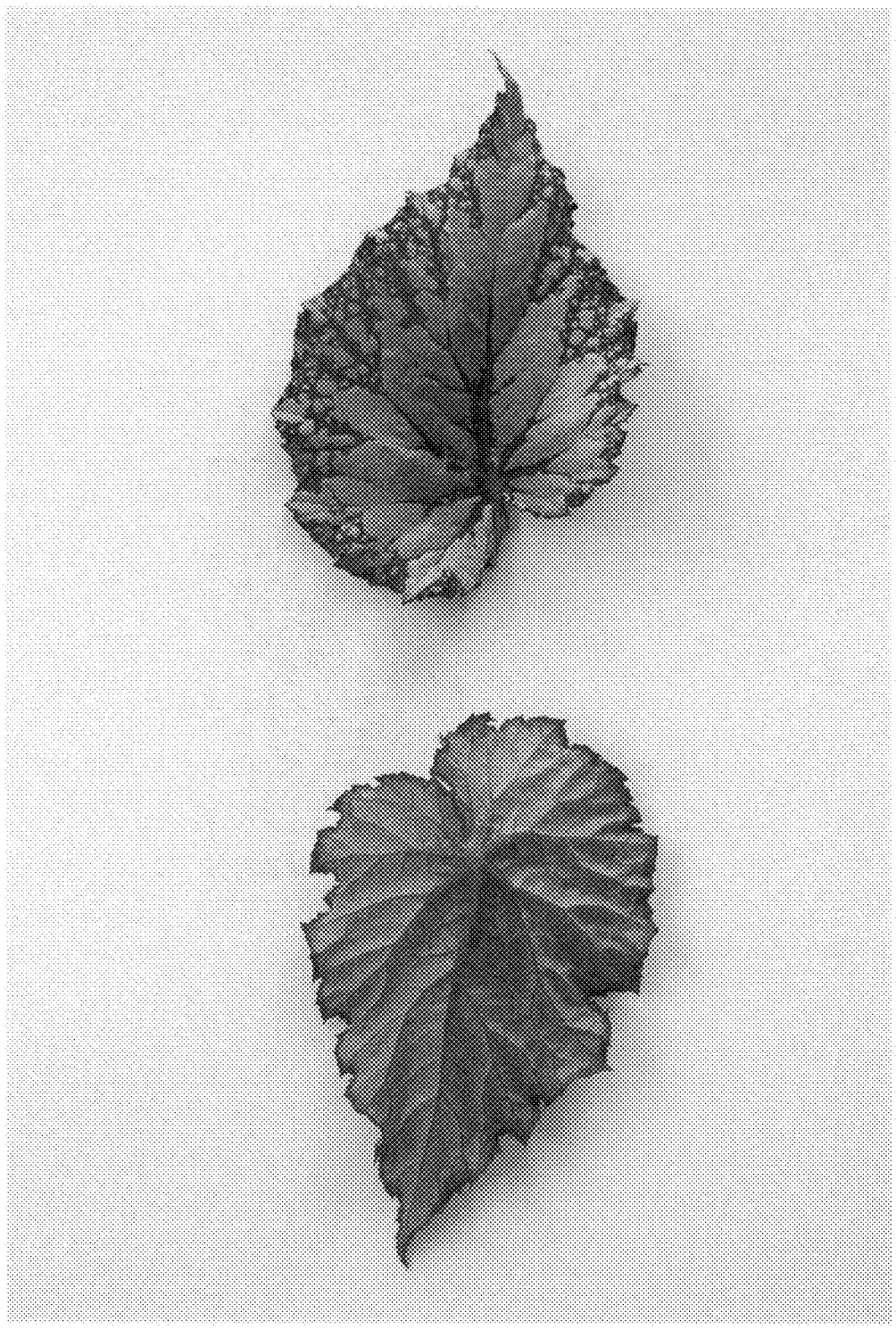

* * * * *